United States Patent [19]
Freed et al.

[11] Patent Number: 6,042,532
[45] Date of Patent: Mar. 28, 2000

[54] PRESSURE CONTROL SYSTEM FOR CARDIAC ASSIST DEVICE

[75] Inventors: Paul S. Freed, Bloomfield Hills; Michael Psakhis, Southfield, both of Mich.

[73] Assignee: L. Vad Technology, Inc., Detroit, Mich.

[21] Appl. No.: 09/036,759

[22] Filed: Mar. 9, 1998

[51] Int. Cl.[7] .................................................. A61M 1/10
[52] U.S. Cl. ............................................................ 600/18
[58] Field of Search .......................................... 600/16–18

[56] References Cited

U.S. PATENT DOCUMENTS

| | | |
|---|---|---|
| 3,553,736 | 1/1971 | Kantrowitz et al. . |
| 3,585,983 | 6/1971 | Kantrowitz et al. . |
| 3,720,199 | 3/1973 | Rishton et al. . |
| 3,877,496 | 4/1975 | Sperberg . |
| 4,004,298 | 1/1977 | Freed . |
| 4,051,840 | 10/1977 | Kantrowitz et al. . |
| 4,077,394 | 3/1978 | McCurdy . |
| 4,092,742 | 6/1978 | Kantrowtz et al. . |
| 4,539,999 | 9/1985 | Mans . |
| 4,630,597 | 12/1986 | Kantrowitz et al. . |
| 4,634,422 | 1/1987 | Kantrowitz et al. . |
| 4,692,148 | 9/1987 | Kantrowitz et al. . |
| 4,733,652 | 3/1988 | Kantrowitz et al. . |
| 4,741,328 | 5/1988 | Gabbay . |
| 4,774,960 | 10/1988 | Arnold et al. . |

(List continued on next page.)

FOREIGN PATENT DOCUMENTS 0 402 872  12/1990  European Pat. Off. .

OTHER PUBLICATIONS

Congestive Heart Failure, © 1994, Springer—Verlag, New York, Inc., Adrian Kantrowitz, Raul R. Cardona, John Au, and Paul S. Freed.

American Journal of Cardiology, © 1988, Intraaortic Balloon Pumping for Prolonged Circulatory Support, Paul S. Freed, MS, Tarik Wasfie, MD, Barina Zado, MD, and Adrian Kantrowitz, MD.

Surgery, © 1969, A Dynamic Aortic Patch as a Permanent Mechanical Auxiliary Ventricle: Experimental Studies, Eduard Sujansky, M.D., Steinar Tjonneland, M.D., Paul S. Freed, M.S., Adrian Kantrowitz, M.D.

(List continued on next page.)

*Primary Examiner*—William E. Kamm
*Attorney, Agent, or Firm*—Young & Basile, P.C.

[57] ABSTRACT

A control system for an inflatable chamber operably positionable with respect to an aorta of a patient monitors an actual flow duration time for inflating and/or deflating the inflatable chamber with a predetermined volume of pressurized fluid and compares the actual flow duration time to a target flow duration time. The system controls the fluid pressure in a high pressure reservoir, and/or in a vacuum reservoir, based on the results of the comparison. If the actual time for inflation is too short compared to the target time, the fluid pressure in the high pressure reservoir is reduced. If the actual time for inflation is too long compared with the target time, the fluid pressure in the high pressure reservoir is increased. If the actual time for deflation is too short compared to the target time, the vacuum in the vacuum reservoir is decreased. If the actual time for deflation is too long compared with the target time, the vacuum in the vacuum reservoir is increased. The incremental step change in fluid pressure within either reservoir can be controlled within predetermined minimum and maximum values, and/or based on the magnitude of the difference between the actual and target time intervals. The change in fluid pressure within either reservoir can be controlled by the system manipulating a control valve, or varying the speed of the compressor, or any combination of the two, until the new calculated value is reached within the reservoir.

31 Claims, 6 Drawing Sheets

U.S. PATENT DOCUMENTS

| | | |
|---|---|---|
| 4,781,715 | 11/1988 | Wurzel . |
| 4,782,817 | 11/1988 | Singh et al. . |
| 4,785,795 | 11/1988 | Singh . |
| 4,809,681 | 3/1989 | Kantrowitz et al. . |
| 4,810,246 | 3/1989 | Frisch et al. . |
| 4,877,035 | 10/1989 | Bogen et al. . |
| 4,888,011 | 12/1989 | Kung et al. . |
| 4,902,272 | 2/1990 | Milder et al. . |
| 4,974,774 | 12/1990 | Nakagawa et al. . |
| 5,045,051 | 9/1991 | Milder et al. . |
| 5,089,016 | 2/1992 | Millner et al. . |
| 5,135,488 | 8/1992 | Foote et al. . |
| 5,139,508 | 8/1992 | Kantrowitz et al. . |
| 5,158,529 | 10/1992 | Kanai ........................................ 600/18 |
| 5,169,379 | 12/1992 | Freed et al. . |
| 5,201,755 | 4/1993 | Klement . |
| 5,219,326 | 6/1993 | Hattler . |
| 5,242,374 | 9/1993 | Isoyama et al. . |
| 5,242,415 | 9/1993 | Kantrowitz et al. . |
| 5,352,180 | 10/1994 | Candelon et al. . |

OTHER PUBLICATIONS

Transplantation Proceedings, © 1971, Current Status of Intraaortic Balloon Pump and Initial Clinical Experience With Aortic Patch Mechanical Auxiliary Ventricle, Adrian Kantrowitz, Joseph S. Krakauer, George Zorzi, Melvyn Rubenfire, Paul S. Freed, Steven Phillips, Marc Lipsius, Claudio Titone, Philip Cascade, and Dov Jaron.

Journal of Biomedical Materials Research, © 1978, Biocompatibility Tests of Components of an Implantable Cardiac Assist Device, Andreas F. Von Recum, Hiroji Imamura, Paul S. Freed, Adrian Kantrowitz, Shan–Te Chen, Merlin E. Ekstrom, Charles A. Baechler and Marion I. Barnhart.

Trans. Amer. Soc. Artif. Int. Organs, © 1972, Initial Clinical Experience with a New Permanent Mechanical Auxiliary Ventricle: The Dynamic Aortic Patch, Adrian Kantrowitz, J. Krakauer, M. Rubenfire, D. Jaron, P.S. Freed, W. Welkowitz, P. Cascade, W. J. Wajszczuk, M. Lipsius, M. Ciborski, S. J. Phillips, and M. T. Hayden.

American Journal of Nursing, © 1973, Care of a Man with a Partial Artificial Heart, Roberta Nelson, Judy Smith, Ruth Drummond, Hilde Pollard Joyce Billingsley, Miriam Nikkila.

PRESSURE CONTROL SYSTEM FOR CARDIAC ASSIST DEVICE

FIELD OF THE INVENTION

The invention relates to a pressure control system for a cardiac assist device.

BACKGROUND OF THE INVENTION

Congestive heart failure remains one of the major causes of mortality and morbidity in the general population and is growing in magnitude. It affects more than 2 million Americans and consumes several billion dollars in hospitalization. Numerous well-controlled randomized trials have shown that, in many cases, vasodilator therapy has not only improved the quality of life in these patients but has prolonged their survival as well. Nevertheless, a sizeable subset of patients in chronic heart failure do not respond to pharmacologic therapy. Furthermore, while cardiac transplantation has developed into an effective treatment modality for end-stage cardiac failure, its wide application has been limited by the inadequate supply of donor hearts. Therefore, effective therapy which improves the quality of life of these patients while simultaneously increasing their longevity remains a major challenge.

It is known in the art how to provide cardiac assistance by positioning a cardiac assist device such as a pump or balloon into the descending thoracic aorta of a patient and causing the device to inflate and deflate in accordance with the natural rhythm of the patient's heart. The device is made to inflate during diastole and deflate during systole. This reduces the load on the heart and raises aortic pressure to increase blood pressure overall and more especially to the coronary arteries. Furthermore, the stroke of the device operates under various types of conditions and pressures corresponding to the changing arterial pressure of the patient. It is desirable that the device inflates and deflates at its intended rate synchronized to the patient's heart.

In addition, it is desirable to prevent the overinflation of the device. It is desirable that the device be constructed of biocompatible materials and include sufficient safeguards to insure the intended operation under circumstances corresponding to the expected range of operation for the device.

SUMMARY OF THE INVENTION

The invention provides a driving and control system for inflatable chambers, such as balloons and pumps for cardiac assist devices, by determining the inflation duration and adjusting the pressure stored in at least one reservoir accordingly. The invention is applicable to a permanent blood pump that is sutured into the wall of the descending thoracic aorta, as well as a temporary balloon pump introduced into the aorta in the vicinity of the heart. In the first configuration, a flexible internal fluid conduit is implanted in a patient and extends from an implanted internal permanent blood pump device to a percutaneous access device (PAD) implanted beneath and projecting through the patient's skin. The PAD allows the implanted pump device to be operatively connected to or disconnected from an external gas handling means and control means. In the second configuration, a temporary balloon pump can be inserted into the descending thoracic artery through the femoral artery of a patient's leg. The temporary balloon pump has a relatively thin flexible tube extending externally of the patient through the incision in the patient's leg for connection to a drive means including an external fluid handling means and control means. In either case, an elongated fluid conduit is provided and connected at one end to an inflatable member disposed within or connected to a patient's descending thoracic aorta and connectible to drive means for controlling inflation and deflation cycles of the inflatable member at an opposite end.

The control means measures arterial pressure of the patient for a specific number of heartbeats during a scheduled pressure measurement procedure. The control means adjusts the inflation and deflation rates of the pump for subsequent heartbeats in accordance with a ventricle assist program stored in memory of the control means based on the arterial pressure measured during the scheduled pressure measurement. The fluid handling means inflates and deflates the inflatable chamber or pumping bladder in accordance with the evaluation of the arterial pressure measured by the control means.

The drive means is available in two drive unit configurations. One is a battery powered wearable drive unit and the other is a line powered drive unit capable of continuous operation. The wearable drive unit is designed to be a portable, battery operated drive unit of minimum size and weight. The drive means for both configurations includes means to monitor an ECG signal, pressure sensor means for monitoring the arterial pressure for a specified number of heartbeats, means for detecting the occurrence of the dicrotic notch, and means for measuring the time interval between the detected R wave and the dicrotic notch value. The control means determines if any fluid pressure adjustment for the inflation and deflation of the bladder is required based on measured parameters. The fluid handling means includes filtering means, means for pressurizing and depressurizing the bladder, and valves for regulating the flow of fluid, such as a gas including air, helium or other suitable fluid, to and from the blood pump.

It is believed that the control system according to the present invention is adaptable to either a generally closed fluid drive system (sometimes referred to herein as a "closed loop" system) or a generally open fluid drive system (sometimes referred to herein as an "open loop" system) with minor modifications. In either case, the fluid flow is driven into the inflatable chamber by fluid pressure from a pressure reservoir. In the open loop system, such as the wearable drive unit, the fluid is driven out of the inflatable chamber by the arterial pressure of the patient. In the closed loop system, such as the line powered drive unit, the shuttle fluid flow is drawn out of the inflatable chamber by a combination of vacuum force from a vacuum reservoir and the arterial pressure of the patient. A gradient pressure is preferably maintained in the closed loop system by controlling the amount of pressure in the vacuum reservoir, controlling the amount of pressure in the pressure reservoir, and/or controlling the variable speed of the compressor operating between the vacuum reservoir and the pressure reservoir with a control device for the closed loop system.

For both the open loop system and the closed loop system, an effective fluid pressure to be maintained in the pressure reservoir is initially predetermined to adequately move fluid into the cardiac assist device. The desired fluid pressure or drive pressure is determined based on the volumetric capacity of the inflatable chamber, catheter size and the mean blood or arterial pressure of the patient. For the closed loop system, the reservoirs for the positive and negative pressure sources can be adjusted to specific pressures so that the differential is equivalent to the desired gradient pressure. In both the open and closed loop systems, a higher pressure in the pressure reservoir in the control system results in a faster inflation of the inflatable chamber. The length of time necessary to inflate the blood pump to the target inflation volume is measured for each heart beat. At the end of inflation, the inflation duration is compared with a preset, physician adjustable, target inflation duration or window of acceptable values defined by a minimum acceptable value and a maximum acceptable value.

For both the open and closed loop systems, the difference between the actual inflation duration and the target inflation duration is used as a feedback signal for pressure regulation in the pressure reservoir. An actual inflation duration that is less than the target inflation duration (minimum acceptable value) indicates that the air pressure in the pressure reservoir is too high. If the actual inflation duration time is less than a minimum acceptable value, then the pressure in the pressure reservoir is too high, and the control program stored in memory of the control means reduces the pressure gradient by performing at least one of the following: actuating a normally closed valve connected to the pressure reservoir to reduce pressure in the pressure reservoir and/or reducing the variable speed of the compressor. In a closed loop system, if the actual inflation duration time is longer than the target inflation duration (maximum acceptable value), then the pressure in the pressure reservoir is too low, and the control program stored in memory of the control means increases the pressure gradient by performing at least one of the following: actuating a normally closed valve in the vacuum reservoir to reduce vacuum in the vacuum reservoir (which correspondingly increases pressure in the pressure reservoir) and/or increasing the variable speed of the compressor. In an open loop system, if the actual inflation duration time is longer than the target inflation duration (maximum acceptable value), then the pressure in the pressure reservoir is too low, and the control program stored in memory of the control means actuates the variable speed compressor to increase pressure in the pressure reservoir. If the actual inflation duration time is between the minimum and maximum acceptable values (i.e. within the physician set window of acceptable values), no action is required by the control program to modify the pressure in the pressure reservoir.

For the open loop system, the motor speed can be adjusted to run a compressor that regulates the pressure in the pressure reservoir. A direct current (DC) electrical motor runs the compressor to create the air pressure in the reservoir. Higher voltage (higher duty cycle) supplied to the motor results in higher motor speed and yields a higher pressure in the reservoir. The air in the reservoir is used to inflate the inflatable chamber of the blood pump and higher reservoir pressure causes faster inflation.

The length of time necessary to inflate the inflatable chamber, such as a blood pump, to the target inflation volume is measured for each heart beat. At the end of inflation, the inflation duration is compared with a preset target inflation duration or preset minimum and maximum target inflation duration. This target can be adjusted by the physician to better fit the individual patient's needs (between 60 and 160 msec, with a default value of 130 msec). The low and high safety limits can not be overwritten by the physician.

The difference between actual inflation duration and the target inflation duration is used as a feedback signal for regulation of pressure in the pressure reservoir. An actual inflation duration less than the target inflation duration (minimum acceptable value) indicates that the fluid pressure in the reservoir is too high, and should be decreased. An actual inflation duration greater than the target inflation duration (maximum acceptable value) indicates that the reservoir pressure is too low and should be increased. The magnitude of the difference between actual duration and target duration is used to determine the size of the step change in pressure to be made in the pressure reservoir.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

The present invention relates to an apparatus and method for controlling a cardiac assist device in a patient in order to receive diastolic augmentation. Various diastolic augmentation systems and devices are currently known. The present invention is particularly adapted for use with an inflatable chamber that is permanently or temporarily disposed in a descending thoracic aorta region of a patient. For example, U.S. Pat. No. 4,630,597 issued Dec. 23, 1986 and U.S. Pat. No. 4,051,840 issued Oct. 4, 1977 disclose details of a permanent pump which are incorporated herein by reference, and U.S. Pat. No. 3,585,983 issued Jun. 22, 1971, U.S. Pat. No. 4,692,148 issued Sep. 8, 1987, U.S. Pat. No. 4,733,652 issued Mar. 29, 1988, U.S. Pat. No. 4,809,681 issued Mar. 7, 1989 and U.S. Pat. No. 5,169,379 issued Dec. 8, 1992, each disclose details of a temporary intra-aortic balloon pump which are also incorporated herein by reference.

Figure 1:
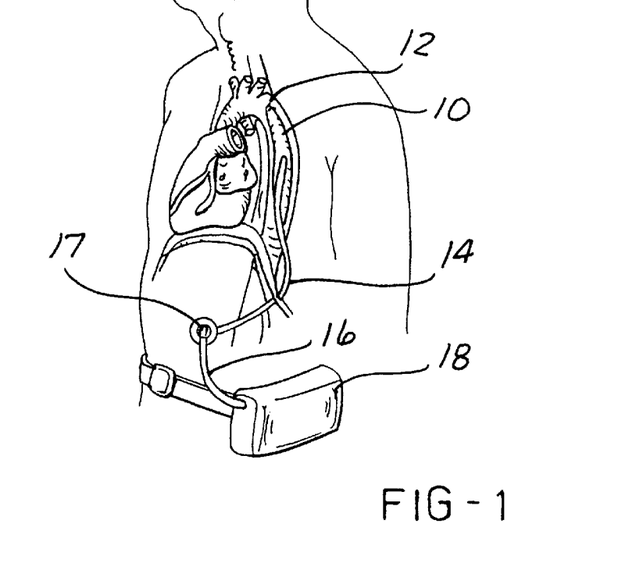
FIG. 1 is a schematic view of major components of a cardiac assist device connected to drive means for controlling the device according to the present invention.
Figure 3:
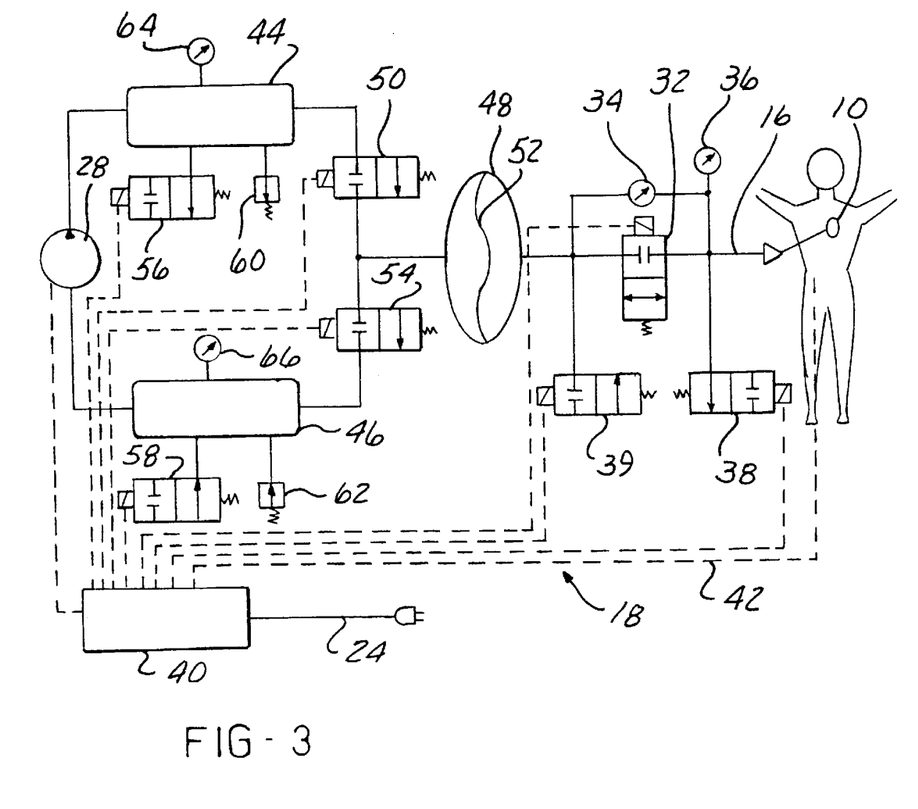
FIG. 3 is a schematic diagram illustrating the general features of a line powered system for operating the cardiac assist device.
Figure 4:
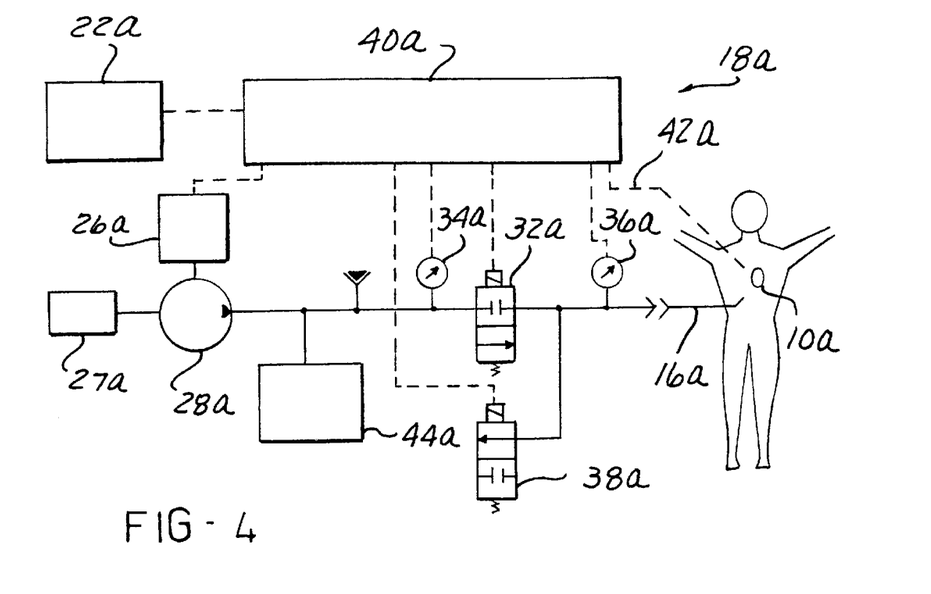
FIG. 4 is a schematic diagram illustrating the general features of a wearable drive system for operating the cardiac assist device.

Major components of one type of a cardiac assist system are shown in FIGS. 1, 3 and 4. In the preferred embodiment, a permanent blood pump 10, 10a is sutured into the wall of the descending thoracic aorta 12. An internal drive line or flexible fluid conduit 14 is operably connected between the implanted inflatable chamber device 10, 10a and a percutaneous access device (PAD) 17 implanted beneath and projecting through the patient's skin, typically in the abdominal area. An external device line or flexible fluid conduit 16, 16a may be operatively connected to or disconnected from an external drive means 18, 18a for controlling cyclical diastolic augmentation. The drive means 18, 18a generally includes a controller and fluid handling means. The drive means 18, 18a conveys pressurized fluid, such as air, to power and to control the timing of inflation and deflation of an inflatable chamber 10, 10a, such as a permanently implanted blood pump or a temporarily inserted balloon pump. There are two configurations of drive means 18, 18a illustrated with respect to the present invention, a line-powered unit 18 (FIG. 3), and wearable battery-powered unit 18a (FIG. 4). Each drive means 18, 18a uses an electrocardiogram (ECG) signal 42, 42a for synchronization.

In the closed loop system of FIG. 3, fluid pressure in the high pressure reservoir 44 is initially set to a sufficient pressure to maintain an adequate inflation time interval for the blood pump 10. The fluid pressure or drive pressure required depends on the fluid conduit size and the volumetric capacity of the blood pump 10. The blood pressure of the patient can be monitored to provide a mean aortic pressure. The initial fluid pressure within the high pressure reservoir during startup of the system can be a predetermined value that is modified according to a control program stored in memory of the control means 40 in response to readings from a pressure measurement procedure conducted on the patient to determine the current blood pressure values of the patient. If the patient's blood pressure rises, the fluid pressure in the high pressure reservoir can be increased according to the control program stored in memory, and if the patient's blood pressure decreases, the fluid pressure in the high pressure reservoir can be decreased according to the control program stored in memory.

In the closed loop system of FIG. 3, a standard line voltage 24 provides a continuous source of power for the line powered drive unit (LPDU). The line powered drive unit is capable of continuous operation. The line powered drive unit may also include a battery backup system (not shown) to maintain operation in the event of mains power interruptions. The LPDU system can operate on the backup battery for up to 6 hours. The closed loop system is driven by the pressure differential between a high pressure reservoir 44 and a lower pressure reservoir or vacuum reservoir 46. An isolation chamber 48 is fluidly connected to the two reservoirs and functions to provide increased safety features with respect to the fluid medium for driving the cardiac assist device. The closed loop drive system illustrated in FIG. 3 can be used with an intra-aortic balloon pump for temporary left ventricular assistance, where the inflatable balloon or chamber is mounted on a catheter and inserted percutaneously usually via the femoral artery into the descending aorta. The balloon catheter is connected to the closed loop drive system, such as that illustrated in FIG. 3 which provides pneumatic power, to drive the shuttle drive fluid back and forth with respect to the inflatable balloon or chamber. The fluid power medium in the temporary intra-aorta balloon pump is usually a helium based closed loop system rather than an air based drive unit. The helium shuttle drive fluid is preferred with the temporary intra-aorta balloon pump due to the smaller diameter of the catheter connecting to the intra-aortic balloon, than is used to connect the permanently implanted blood pump 10 to the percutaneous access device 17.

Figure 5:
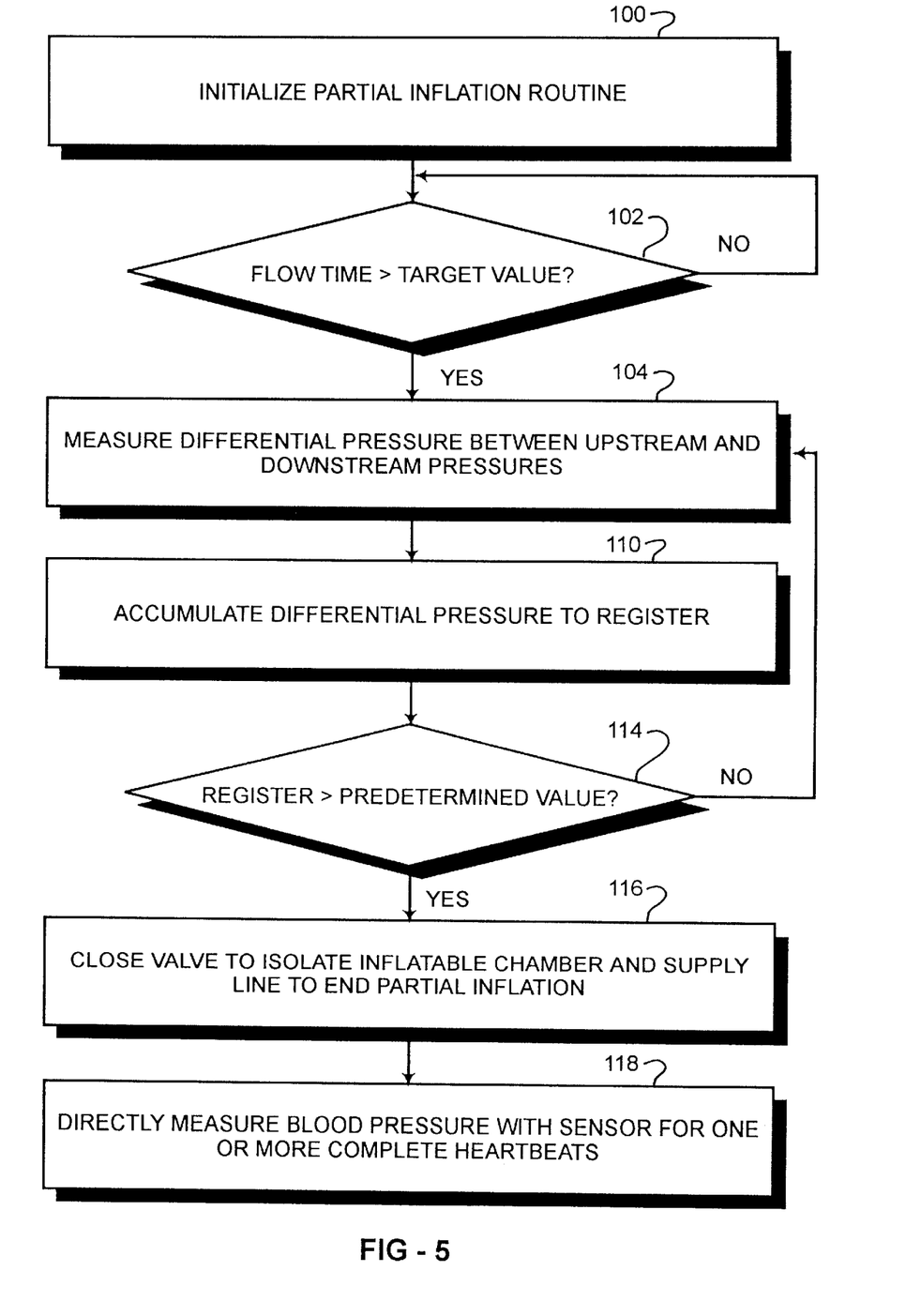
FIG. 5 is a simplified flow chart illustrating a partial inflation routine for blood pressure measurement.

The control means 40 can include a central processing unit (CPU) or a microprocessor controlling a compressor 28 to generate the amount of pressurized fluid necessary to inflate the inflatable chamber, such as blood pump 10, at the patient's current heart rate and blood pressure. The blood pressure is measured directly, using a control program including the steps as shown in FIG. 5 and discussed further hereinafter. The control program monitors and accumulates the differential pressure across a valve aperture over the time required to introduce a fixed quantity of pressurized fluid into the inflatable chamber. The control means 40 also monitors system operation and safely terminates pumping if a malfunction is detected.

Figure 2:
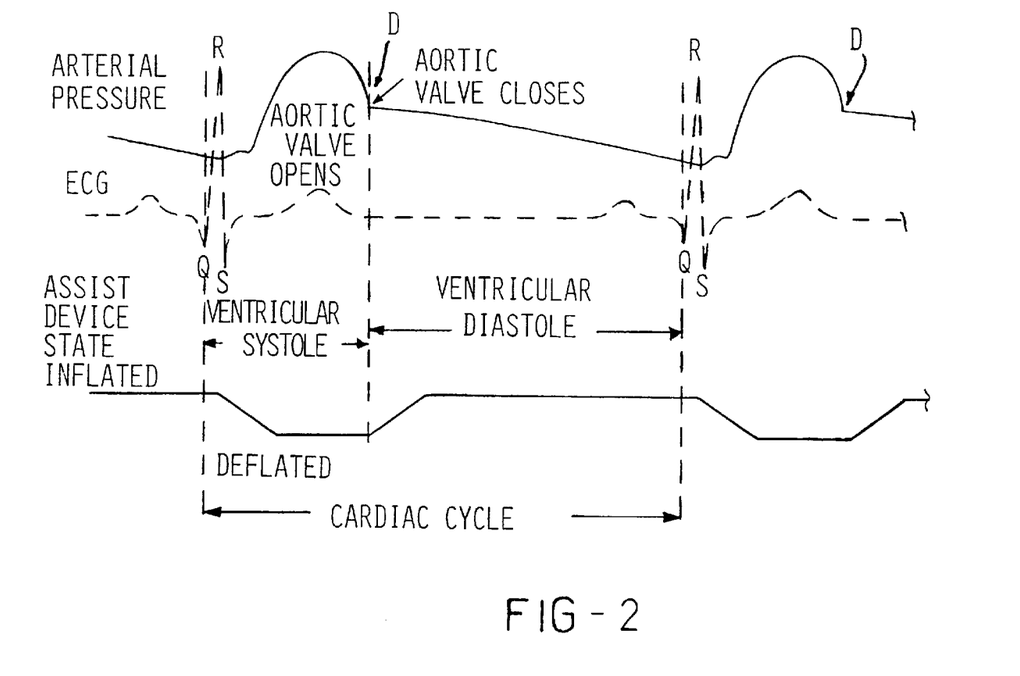
FIG. 2 is a graph showing the relationship of normal aortic blood pressure without assist, the ECG signal and assist device inflation state.

The control means 40 is optimized for real time signal processing and control applications. As illustrated in FIG. 3, the pressure sensors and ECG input are part of a control system for shuttling gas to/from the blood pump 10 according to the opening and closing of the aortic valve as seen in FIG. 2. A typical power up sequence can include one or more of the steps described below. After power is switched on, an initialization and self test procedure is executed. Computer memory, processor operation, software integrity, safety control system, sensors, valves, and compressor output are checked. The initialization also places the valves in a safe state before pumping begins. The patient ECG is then sampled and trigger information is calculated. This becomes the time base for subsequent event detection and valve timing. Blood pressure is measured using a control program illustrated in a simplified flow chart in FIG. 5. The blood pump 10 is partially filled with gas and allowed to settle. This settling equalizes pressures on either side of the membrane, which then acts as a pressure sensor. No pumping takes place preferably for two beats to allow waveform analysis. Then pumping begins with up-to-date patient information. The detection of events can be overridden by a physician if the patient has special needs. This information is stored in non-volatile memory of the control means 40. Pumping continues with the defined parameters until another timing update is mandated. This is done at regular intervals, or if needed due to changing patient conditions. Pumping can be terminated by disconnecting the drive line, shutting the unit off, or running the batteries down to their end discharge point. Disconnection or low battery results in an error code that is meant to inform the user of actions required to continue pumping.

Drive unit function can be monitored through a high speed serial connection, either locally or remotely via modem. Patient waveforms and drive unit status can be displayed on a standard PC running DOS. Under the direction of a physician, patient parameters that pertain to timing settings and error limits can be updated as appropriate for a particular patient. Also the history of drive unit function for a particular patient can be uploaded for analysis via the above described serial port. This history includes all error conditions encountered, unusual patient conditions, drive unit and patient state at the time of the error, and run time of the unit. This data can be used to adjust the drive unit to the patient, indicate the need for additional training of the patient in the operation of the drive unit, demonstrate erroneous operation, and suggest maintenance when service intervals are exceeded.

Referring to FIG. 3, the features of the is driver according to the line powered embodiment of the present invention is a closed loop system for operating the inflatable chamber 10. The output side of the compressor 28 is fluidly connected to a high pressure reservoir 44 capable of maintaining a desired pressure for fluid stored within the reservoir. The pressure within the reservoir 44 can be varied by the control means 40 in response to measured parameters. The output side of the high pressure reservoir 44 is fluidly connected to switching valve means, such as a normally closed two-way solenoid valve 50, for controlling flow of pressurized fluid from reservoir 44 to an isolator 48. The output side of switching valve means 50 is connected to the isolator 48 via a drive line. A flexible diaphragm 52 separates the fluid in the drive chamber from a fixed amount of shuttle fluid on the driven chamber or patient side used to inflate the inflatable chamber 10. For a temporary intra-aortic balloon pump introduced in the thoracic aorta via the patient's femoral artery, the shuttle gas preferably is helium. For a permanently implanted blood pump sewn into the wall of the thoracic aorta, the shuttle gas preferably is air. It is expected that the present invention would not be limited by the type of pressurized fluid used to inflate the inflatable chamber or to drive the inflation process and in fact any suitable fluid, preferably in gaseous form, such as air, could be used with satisfactory results.

The isolator includes two rigid disks or cups sealed together to form a chamber. The isolator has an input chamber and an output chamber. The movable and flexible diaphragm 52 disposed in the isolator separates the input chamber from the output chamber. A sufficient amount of fluid is provided in the input chamber and the output chamber to ensure proper operation of the system.

On the input side of the compressor 28 is a low pressure reservoir or vacuum reservoir 46. The amount of pressure or vacuum in the reservoir 46 is controlled by the control means 40 in response to measured parameters, and can be varied. The input side of the variable vacuum reservoir is fluidly connected to switch valve means, such as a two-way normally closed solenoid valve 54 for controlling flow of pressurized fluid out of the chamber 48. The switching valve means 54 is fluidly connected to the input chamber of isolator 48 via the drive line. The compressor 28 for the closed loop system illustrated in FIG. 3 is preferably a variable speed compressor that maintains the desired fluid pressure in the high pressure reservoir 44. Preferably, the variable speed compressor 28 of the closed loop system maintains a desired differential pressure ΔP between the high pressure reservoir 44 and the low pressure reservoir 46 depending on patient parameters, even though the pressure in each reservoir may be varying in response to the control means 40.

The control system according to the present invention as illustrated in FIG. 3 is a closed system wherein fluid, such as air, is pumped by the compressor 28 from the low pressure reservoir 46 to the high pressure reservoir 44. The high pressure reservoir 44 is selectively connected to the input chamber of the isolator 48 by the control means 40 actuating switch valve means 50. The pressurized fluid delivered to the input chamber is then selectively routed back from the input chamber by the control means 40 actuating switch valve means 54 to connect to the vacuum reservoir 46 during a contracting segment or deflation portion of the cycle of the inflatable chamber 10.

If it is desirable to decrease the pressure in the high pressure reservoir 44 or increase the vacuum in the low pressure reservoir 46, it can be accomplished by the control means 40 selectively actuating individual normally closed solenoid valves 56, 58 extending to atmosphere from the high pressure reservoir 44 and low pressure reservoir 46 respectively. In the line powered embodiment, solenoid valve 56 can be opened to expel pressurized fluid, such as compressed air, from the system to lower the positive pressure in pressure reservoir 44. Solenoid valve 58 can be opened to add fluid, such as air, to the system to increase the positive pressure reservoir 44.

When switch valve means 50 is open and switch valve means 54 is closed, positive pressure delivers pressurized fluid, such as air, into the input chamber of isolator 48. As a result when control valve 32 is opened, movable member 52 moves toward the output chamber. During this period of time, shuttle fluid, such as a gas, in the output chamber passes through shuttle switching control valve 32 and inflates inflatable chamber 10. Shuttle switching control valve 32, which will be discussed further, acts as a metering orifice for measuring the volume of fluid passing through the control valve 32. The flow duration time interval required to deliver a predetermined volume of pressurized fluid to the inflatable chamber 10 is also monitored. If the switch valve means 54 is open and the switch valve means 50 is closed, pressurized fluid, such as air, in the input chamber will equalize with the low or negative pressure in low pressure reservoir 46. When control valve 32 is opened, movable member 52 of isolator 48 will move toward the input chamber drawing shuttle fluid out of the inflatable chamber 10.

When the normally closed control valve 32 is opened, fluid in the cardiac assist device side of isolation chamber 48 is permitted to flow through the open aperture of shuttle valve 32 in a direction depending on the prevailing pressure in the isolator controlled by the valves 50, 54, and control means 40. Valve 32 is operated between an open position and a closed position in response to the actuation signal generated by control means 40. When switch valve means 50 is open and switch valve means 54 is closed, the isolation chamber 48 is preloaded with pressurized fluid from the closed loop drive system. When shuttle valve 32 is actuated, the preloaded, pressurized isolation chamber 48 drives the moveable member 52 in one direction to force fluid through the open aperture of shuttle control valve means 32 into the inflatable chamber 10. Shuttle control valve means 32 can then be de-energized to isolate the inflatable chamber from the drive means. Switch valve means 50 is then closed and switch valve means 54 is opened to draw fluid out of the isolation chamber 48 to preload the isolation chamber 48 with vacuum. When the shuttle control valve means 32 is opened, the vacuum-preload isolation chamber 48 draws fluid out of the inflatable chamber 10. The preloading of the isolation chamber 48 cyclically with pressure and vacuum assists in decreasing the response time of the inflatable chamber 10 allowing for faster inflation and deflation. Valve 38 is provided as a safety feature to permit expulsion of fluid from the inflatable chamber 10 in the case of drive unit failure. A second valve 39 is located between the isolation chamber 48 and control valve means 32 for adding shuttle fluid to the system through the fluid conduit. Pressure sensor 34 measures differential pressure across control valve means 32 in FIG. 3, whereas pressure sensor 34a is positioned upstream of control valve means 32a in FIG. 4. In FIG. 4, pressure sensor 36a is positioned downstream with respect to shuttle control valve means 32a to measure differential pressure across control valve means 32a in either direction of fluid flow in combination with pressure sensor 34a. Shuttle control valve means 32 functions as a metering orifice so that pressure sensor 34 indicates differential pressure across control valve means 32 during inflation and deflation. Pressure sensor 36 operates to indicate pressure within the inflatable chamber when isolated from the drive unit by closure of control valve means 32.

The system of FIG. 3 is operated according to a control program stored in memory of the control means 40. The compressor 28 charges the positive pressure reservoir 44 according to the patient's heart rate and diastolic pressure to a level sufficient to provide full inflation of the blood pump. A spring loaded pressure relief valve 60 communicating with high pressure reservoir 44 and spring loaded pressure relief valve 62 communicating with low pressure reservoir 46 ensure that the respective reservoir pressures stay within safe limits. These mechanical pressure relief valves 60, 62 provide redundant backup in case of controller failure. Normally the control means 40 maintains the desired fluid pressure in high pressure reservoir 44 by controlling the selective opening and closing of valves 56 and 58 connected to the high pressure reservoir 44 and low pressure reservoir 46 respectively. However, if the patient's heart rate drops dramatically, the pressure could rise, temporarily, to the bleed setting on the relief valve 60. Also, the control means 40 continually monitors the pressure in the high pressure reservoir 44 and can shut the system down in the event that the pressure exceeds the bleed setting.

The switch valve means 50 and 54, control valve means 32 and fluid pressure control the inflation/deflation cycles of the inflatable chamber 10 in the system. Inflate switch valve means 50 fluidly connects the reservoir 44 to the drive line and to isolation chamber 48. The control means 40 monitors and accumulates a value corresponding to the volume of the fluid flow through the open fixed aperture of shuttle control valve means 32 when opened. The inflate switch valve means 50 is preferably closed when inflation is complete, or after a fixed maximum delay. Deflate switch valve means 54 draws fluid from the isolation chamber 48 to the low pressure reservoir 46. When shuttle control valve means 32 is opened while vacuum is applied to the isolation chamber 48, fluid is drawn out of the inflatable chamber 10.

The length of time necessary to inflate the inflatable chamber 10 with a target inflation volume is measured for each heart beat. At the end of inflation, the actual inflation flow duration time interval is compared with a preset target inflation flow duration time interval. This target can be adjusted by the physician to better fit the individual patient's needs. The target inflation flow duration time interval has low and high safety limits of 80 msec and 150 msec, respectively, which can not be overwritten by the physician.

The difference between the actual inflation duration and the target inflation duration is used as a feedback signal for pressure change in the closed loop control system. The sign of the difference tells the computer 40 in what direction the pressure should be changed by adjusting the appropriate pressure reservoir. A negative sign indicates that actual inflation duration is less then target inflation duration. Therefore, the fluid pressure in the high pressure reservoir 44 is too high. A portion of the pressure in the high pressure reservoir 44 can be expelled by the control means 40 opening valve 56 to bleed some fluid pressure out of the high pressure reservoir 44; and/or the pressure gradient between the high pressure reservoir 44 and the low pressure reservoir 46 can be decreased by decreasing the variable speed of the compressor 28. Oppositely, a positive sign indicates that actual inflation time is greater than the target inflation time. Therefore, the pressure in high reservoir pressure 44 is too low and the low pressure in the vacuum pressure reservoir 46 can be increased or raised, so that pressure in the high pressure reservoir 44 increases. This can be accomplished by the control means 40 opening valve 58 to bleed some fluid into low pressure reservoir 46 thereby reducing the vacuum pressure and increasing the pressure of the high pressure reservoir 44 through the work of compressor 28; and/or by increasing the pressure gradient between the high pressure reservoir 44 and the low pressure reservoir 46 by increasing the variable speed of the compressor 28. The absolute value of this difference is used to determine the magnitude of the incremental change, preferably within predefined minimum and maximum step values, to the appropriate pressure reservoir and/or to the variable speed setting of the compressor 28.

Overall, an inflation volume and inflation speed control program monitors the volume of the fluid flow into the inflatable chamber 10 and gives a signal when to stop inflation. The inflation duration is used to determine whether a pressure change is required to keep the inflation duration close to its optimal physician set value or within minimum and maximum physician set values. When the control program stops the inflation, it also determines whether to change the pressure in the high pressure reservoir 44 by opening either valve 56 or valve 58, and/or to change the pressure gradient by either increasing or decreasing the variable speed of the compressor 28, 28a.

FIG. 5 shows a simplified flow chart for the control program of controller 40 when inflating pump 10 to a predetermined volume. Step 100 initializes the partial inflation routine of the program to partially inflate cardiac assist device 10 to a predetermined volume, typically including setting storage registers to zero and other values to their respective defaults. Deflation valve 54 has been closed previously. Inflation valve 50 has been opened previously and then control valve 32 is opened to begin inflating the inflatable chamber. The flow time is compared to a target value in step 102. During inflation, when control valve 32 is open, the control valve 32 functions as a metering orifice. Step 104 measures a differential pressure between upstream pressure sensor 34a and downstream pressure sensor 36a of FIG. 4. For the line power drive unit of FIG. 3, the differential pressure is measured directly by sensor 34. The differential pressure ($\Delta P$) is accumulated over time in a memory register at step 110. Step 110 accumulates the differential pressure measurement corresponding to the accumulated incremental volume to contents of the memory register. The memory register is then evaluated to determine whether the accumulated differential pressure measurements are greater than a predetermined value in step 114. If the memory register is not greater than the predetermined value, the routine returns to step 104. If the memory register is greater than the predetermined value, then the inflatable chamber is sufficiently, partially inflated in order to continue the scheduled pressure measurement procedure.

Within the environment of the patient, the fluid pressure in the partially inflated flaccid pump 10 correspondingly mirrors the arterial pressure. The pressure sensor 36 measures pressure within the partially inflated, inflatable chamber of pump 10 corresponding to the arterial pressure of the patient. Once the pump 10 is partially filled with the predetermined volume of pressurized fluid, the control valve 32 is closed and the pump 10 is allowed to settle in step 116. Settling equalizes pressures throughout the isolated inflatable chamber 10 and on either side of the membrane of pump 10, allowing the isolated inflation chamber 10 to act as a pressure transducer. The controller 40 measures the aortic pressure wave form based on pressure measurements of sensor 36 and takes sample pressure readings approximately every four milliseconds, for at least one cardiac cycle during the scheduled pressure measurement procedure and preferably during two complete cardiac cycles in step 118. Preferably, measurements are taken over two heartbeats to allow verified wave form measurement and analysis.

Based on the stored information of the cardiac cycle, taken during the scheduled pressure measurement procedure, the dicrotic notch (D) can be detected from a reversal of slope occurring within a physician adjusted time window. If not found, detection of negative to zero slope is checked or if that is not found, detection of largest negative slope of a minimum duration is checked. If no notch (D) is detected within the time window, the "Dicrotic notch, default" specified in a patient parameter table stored in the controller 40 is used. The controller 40 also monitors the QRS complex from the ECG signal taken during the scheduled pressure measurement procedure. From this stored information, controller 40 computes the time from the QRS complex or R-wave to the dicrotic notch (D) as the systolic time interval. As a result, pumping begins with up-to-date patient information. The detection of the aforementioned events can be adjusted or overridden by a physician within safety parameter windows, if the patient has special needs. These parameters are stored in the non-volatile memory of the controller 40. Pumping continues with the defined parameters until another timing update is mandated. The scheduled pressure measurement is executed at a time interval of ten minutes as a default, or other programmable time interval ranging from three to twenty minutes. The schedule pressure measurement procedure can be requested ahead of schedule, if the heart rate changes by more than 20%, or other physician programmable change trigger of between 10%–80% inclusive.

Figure 6:
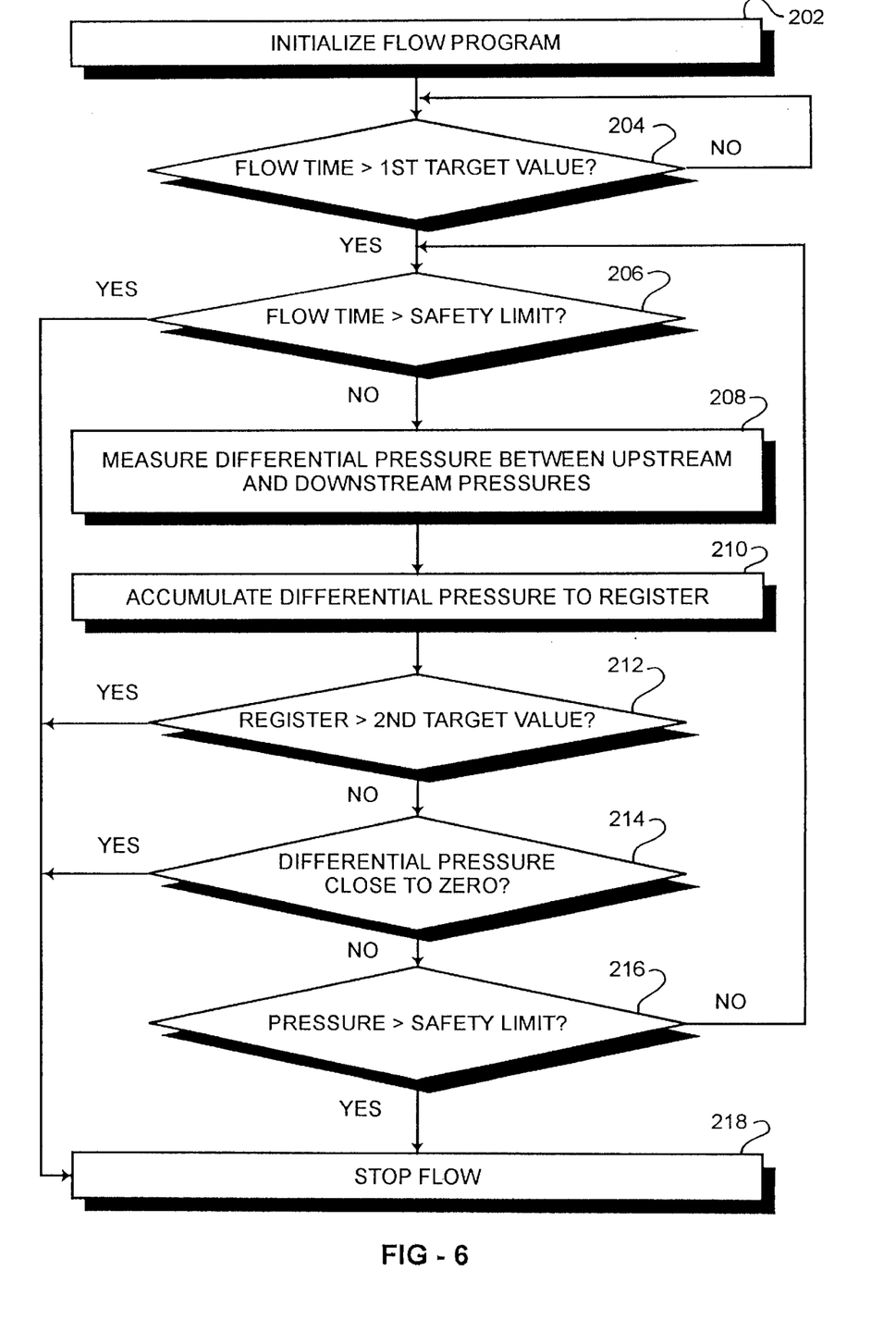
FIG. 6 is a simplified flow chart illustrating control of inflation volume and velocity for the cardiac assist device.

FIG. 6 is a simplified flow chart illustrating the operation of the program stored in memory of the control means. At the beginning of inflation all variables are initialized in step 202. It has been found to take approximately 28 milliseconds for the flow disturbance caused by the opening of the valve means 32 to subside and allow reliable pressure readings for flow determinations. Once the first target value corresponding to this predetermined time period has elapsed (step 204), a safety time limit is checked in step 206. If the elapsed flow time has exceeded a predetermined safety limit, valve means 32 is closed to prevent further fluid flow through the fluid conduit to the inflatable chamber 10. Otherwise, the flow measurement routine commences to measure the differential pressure which corresponds to the volume of pressurized fluid passing through valve means 32. The simplified flow chart of FIG. 6, and in particular steps 208, 210 and 212 of the program of control means 40, measures the differential pressure with respect to time to determine a value corresponding to volume of fluid flow passing through the valve means 32 when in an open position. Valve means 32 is opened to begin fluid flow through the fluid conduit leading to the inflatable chamber 10. During fluid flow, when valve means 32 is open, the aperture of the valve means 32 functions as a metering orifice. Step 208 measures a differential pressure measured between the pressure upstream of the valve means 32 and the pressure downstream of the valve means 32. The differential pressure ($\Delta P$) is accumulated in a register at step 210. The register is evaluated to determine whether the accumulated $\Delta P$ corresponding to volume is greater than a predetermined second target value in step 212. If the register is not greater than the predetermined second target value corresponding to a predetermined volume, the routine continues to step 214. If the register is greater than the predetermined second target value, then the second target value has been reached and valve means 32 is moved to a closed position, thereby stopping flow at step 218. In step 214, the program compares the $\Delta P$ to zero to determine if there is sufficient pressure differential to continue fluid flow. If sufficient pressure differential exists to continue fluid flow through the valve orifice, the program continues to step 216. Otherwise, if the pressure differential is close to zero, the program stops flow in step 218. In step 216, the program compares the existing pressure to a safety limit. If the pressure is less than the safety limit, the program continues by returning to a position just before step 206. If the existing pressure is greater than the safety limit, the program stops flow by branching to step 218.

Figure 7:
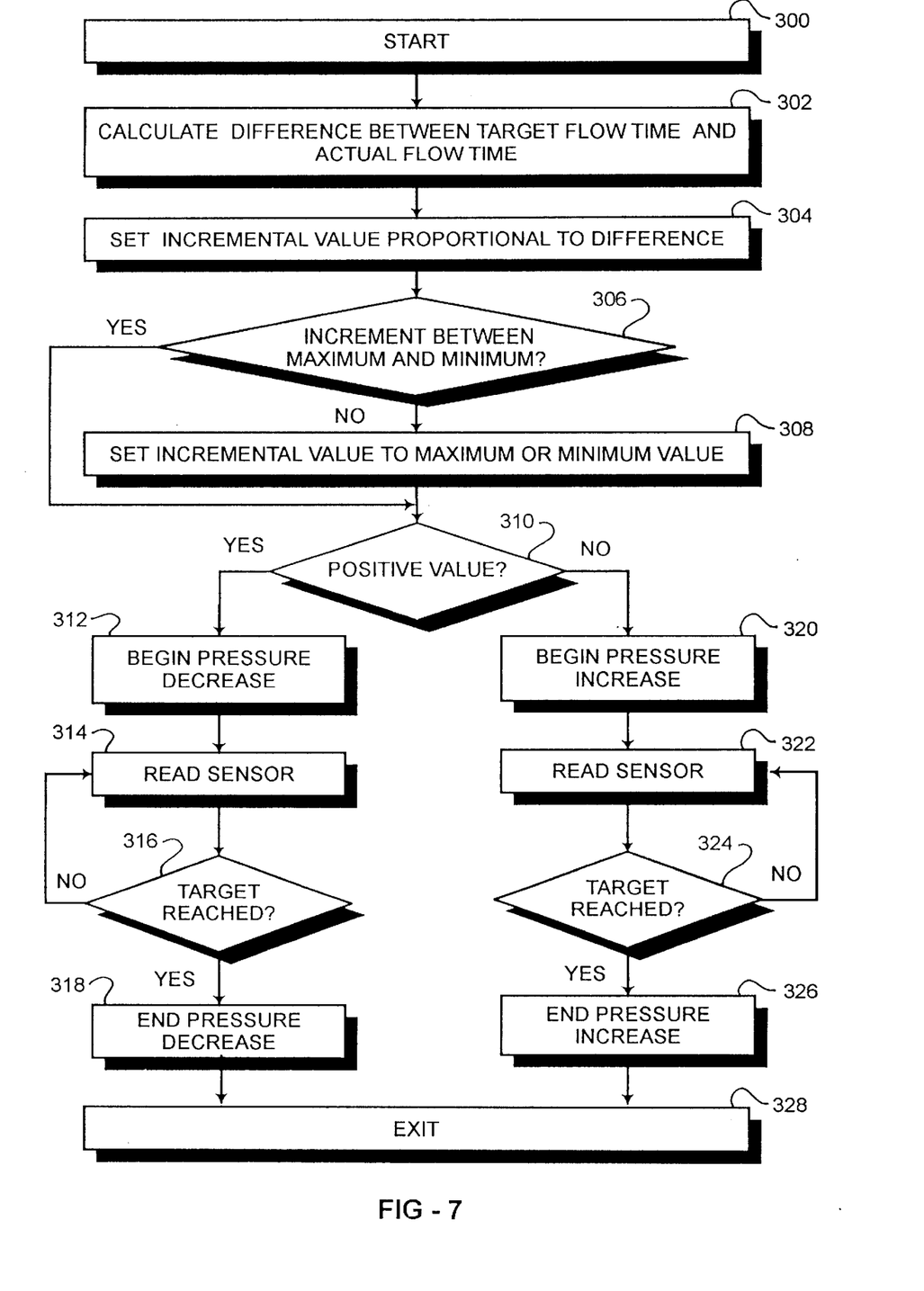
FIG. 7 is a simplified flow chart illustrating a routine to adjust pressure in a positive pressure reservoir to drive fluid to the cardiac assist device.

FIG. 7 is a simplified flow chart to measure and control the flow duration for the subsequent inflation during diastole by adjusting the pressure in the pressure reservoir as a result of selectively opening valves 56, 58 and/or varying the speed of compressor 28, 28a. The routine begins in the start box 300 in FIG. 7. The function of this routine is to change the target high pressure according to a pressure increment determined by the control program based on measured parameters. The increment is preferably proportional to the magnitude of the difference calculated between the actual inflation duration time and a target inflation duration time ($\Delta t$) (steps 302 and 304). In general, the pressure increment determined by the control program is simply added to the previous high pressure target. However, in some situations, the control program will limit the value of incremental pressure changes to prevent unwanted drastic pressure changes or overregulation. The control programs sets the pressure increment to a value proportional to the difference between the actual flow time and the target flow time in step 304. The incremental value is compared to predetermined minimum and maximum acceptable values in step 306, and is adjusted to the minimum or maximum incremental value if the value exceeded the acceptable limits in step 308.

To prevent overregulation, the routine keeps track of how many consecutive pressure changes were applied in the same direction. If it detects several consecutive pressure changes in the same direction, the control means 40 begins to decrease the magnitude of the pressure increment. As a result, the degree of change in the target value for the high pressure setting is reduced in magnitude before the maximum pressure value is reached. This is desirable to take into account the inertia of the positive pressure, such that the predictive scheme according to the present invention during closed loop control regulation can reduce or eliminate significant oscillations in fluid pressure that could possibly result. Once the pressure increment is corrected as necessary, the increment is used to update the target pressure in the high pressure reservoir 44, 44a. The control means 40, 40a determines if $\Delta t$ is a positive or negative value in step 310 as a result of subtracting the actual inflation duration time from the target inflation duration time in step 302.

If $\Delta t$ is positive, in other words if the target flow time is greater than the actual flow time, the pressure in high pressure reservoir 44, 44a is reduced incrementally in steps 312 through 318 to increase the amount of time required for subsequent inflations. Steps 312 to 318 decrease the pressure in the high pressure reservoir 44, 44a by opening control valve means 56 to release pressure from reservoir 44 and/or by decreasing the variable of speed of the compressor 28, 28a. The pressure sensor 64 is continually monitored by the control program and the control valve means 56 is closed after pressure in the pressure reservoir 44 has decreased to the target value as determined by the incremental change called for in the control program.

If $\Delta t$ is negative, in other words if the target flow time is less than the actual flow time, the amount of vacuum in low pressure reservoir 46 is reduced incrementally in steps 320 through 326 to decrease the amount of time required for subsequent inflations. By reducing the amount of vacuum pressure in the low pressure reservoir or vacuum pressure reservoir 46, the pressure reading increases in the high pressure reservoir 44 due to the operation of the variable speed compressor 28. Steps 320 through 326 open control valve means 58 to add fluid to low pressure reservoir 46.

Pressure sensor 66 is continually monitored by the control program and the control valve means 58 is closed after vacuum in the low pressure reservoir 46 has changed by the incremental pressure to the target value as determined by the control program. Compressor 28 compensates the charge in one reservoir by increasing or decreasing the pressure in the other reservoir so that the differential pressure between the high pressure reservoir 44 and low pressure reservoir 46 remains relatively constant at constant compressor speed.

The differential pressure value between the high pressure reservoir 44 and the low pressure reservoir 46 can be varied by changing the speed of the variable speed compressor 28 with the control program of the control means 40. The control program of the control means 40a can control the pressure setting of the high pressure reservoir 44a by changing the speed of the variable speed compressor 28a according to the steps of FIG. 7. The pressure adjustment routine of FIG. 7 is run at the end of every inflation portion of the inflation/deflation cycle. The pressure adjustment portion of the control program compares the current sensor value of pressure sensor 64, 66 monitoring the pressure reservoirs 44 and 46 respectively with the desired target value. If the target pressure is different from the actual pressure, the pressure in the high pressure reservoir 44 is changed in a direction to decrease the difference. The pressure adjustment routine maintains the current pressure when the pressure reading from the high pressure reservoir 44 equals the target pressure value. Thus, the actual pressure is adjusted incrementally, rather than abruptly, to facilitate smooth operation during pressure regulation.

There are also several safety controls incorporated into the present invention to prevent the inflatable chamber 10 from overinflating. Inflation will be stopped if any one or more of the following conditions occurs: 1) the current value of pressure in the high pressure reservoir 44, 44a is greater than a predetermined safety limit (i.e. compressor and/or safety relief valve malfunction) will cause the drive means 18 to shut down automatically (FIG. 6, step 216); and 2) the current value of inflation duration is longer than the inflation time safety limit (FIG. 6, step 206). That is, if the pressure in the high pressure reservoir is too low to continue to provide inflation of the inflatable chamber 10 (i.e. flow through control valve means 32 essentially equals zero), and therefore the pressure in the high pressure reservoir 44 needs to be increased significantly and differential pressure (pressure across the shuttle inflate control valve means 32) is close to zero (FIG. 6, step 214). This indicates that there is no fluid flow across control valve means 32 because the pressure in the high pressure reservoir 44 is not sufficient to continue to inflate the inflatable chamber 10 against the currently existing blood pressure of the patient, and therefore the pressure in the high pressure reservoir 44 needs to be increased. If the above listed conditions have been encountered, the "stop inflation" flag will be set and the pressure in the high pressure reservoir 44 will be increased incrementally by an amount equal to the predefined maximum incremental value.

Although the closed loop fluid drive system is the preferred embodiment, it is expected that the control system, according to the present invention can be modified for use in controlling an open loop fluid drive system or wearable system as schematically illustrated in FIG. 4. The wearable drive unit of FIG. 4 is designed to be a portable, battery operated drive unit of a minimum size and weight to allow mobility. The battery pack is chosen as a trade-off between weight and operation time. One hour is the nominal operating time on batteries, given charge density limitations of current battery technologies. The wearable drive unit includes a compressor 28a run by motor 26a. A high pressure reservoir 44a communicates with a normally closed control valve means 32a. An upstream pressure sensor 34a and a downstream pressure sensor 36a are positioned in respective positions on either side of control valve means 32a. During inflation, a normally open deflation valve 38a is closed and control valve means 32a is opened to allow passage of pressurized fluid. Control valve means 32a functions as a metering orifice while open allowing fluid to flow through the fixed aperture. Differential pressure across control valve means 32a is measured and cumulatively stored in memory. The accumulated, stored pressure value corresponds to a volume of pressurized fluid entering the inflatable chamber 10a of the blood pump. The normally open deflation valve 38a is deenergized to permit expulsion of pressurized fluid from the inflatable chamber 10a to atmosphere in response to the patient's natural blood pressure deflating the chamber 10a. The control means 40a controls the above components, monitors the ECG signal 42a, as well as provides storage for a control program and information monitored during the pressure measurement procedure.

The primary function of the drive unit 18, 18a of both the battery operated and line power configurations is to inflate and deflate the cardiac assist device 10, 10a synchronously with the patient's natural heart rhythm or ECG, thereby providing diastolic augmentation to the left ventricle of the heart. The drive unit 18, 18a uses an R wave from the ECG signal 42, 42a and data from an aortic pressure measurement to adjust inflation timing. The operation of the control program stored in memory of the control means 40, 40a is exactly the same as previously described and illustrated in FIGS. 5 through 7, with the exception of actuating control valve means 56, 58 to decrease/increase pressure in the high pressure reservoir 44 which is not present in FIG. 4. In the open loop system of FIG. 4, the pressure in the high pressure reservoir 44a is increased by increasing the voltage applied to the DC motor 26a operating the compressor 28a to increase pressure output. If the pressure in high pressure reservoir 44a gets too high, the pressure can be reduced by decreasing the voltage applied to the DC motor 26a operating the compressor 28a, or a control valve (not shown) can be connected to reservoir 44a to expel excessive fluid pressure. Upstream pressure sensors 34a can be used to monitor pressure within high pressure reservoir 44a when the control valve means 32a is closed. Any changes to pressure reservoir 44a can be accomplished by adjusting the speed of the compressor 28a to increase and/or decrease pressure in reservoir 44a, or the control valve (not shown) can be used to lower the pressure in the high pressure reservoirs 44a. Battery 22a supplies power to the control means 40a and motor 26a. The compressor 28a preferably includes a filter 27a on the intake line.

Figure 8:
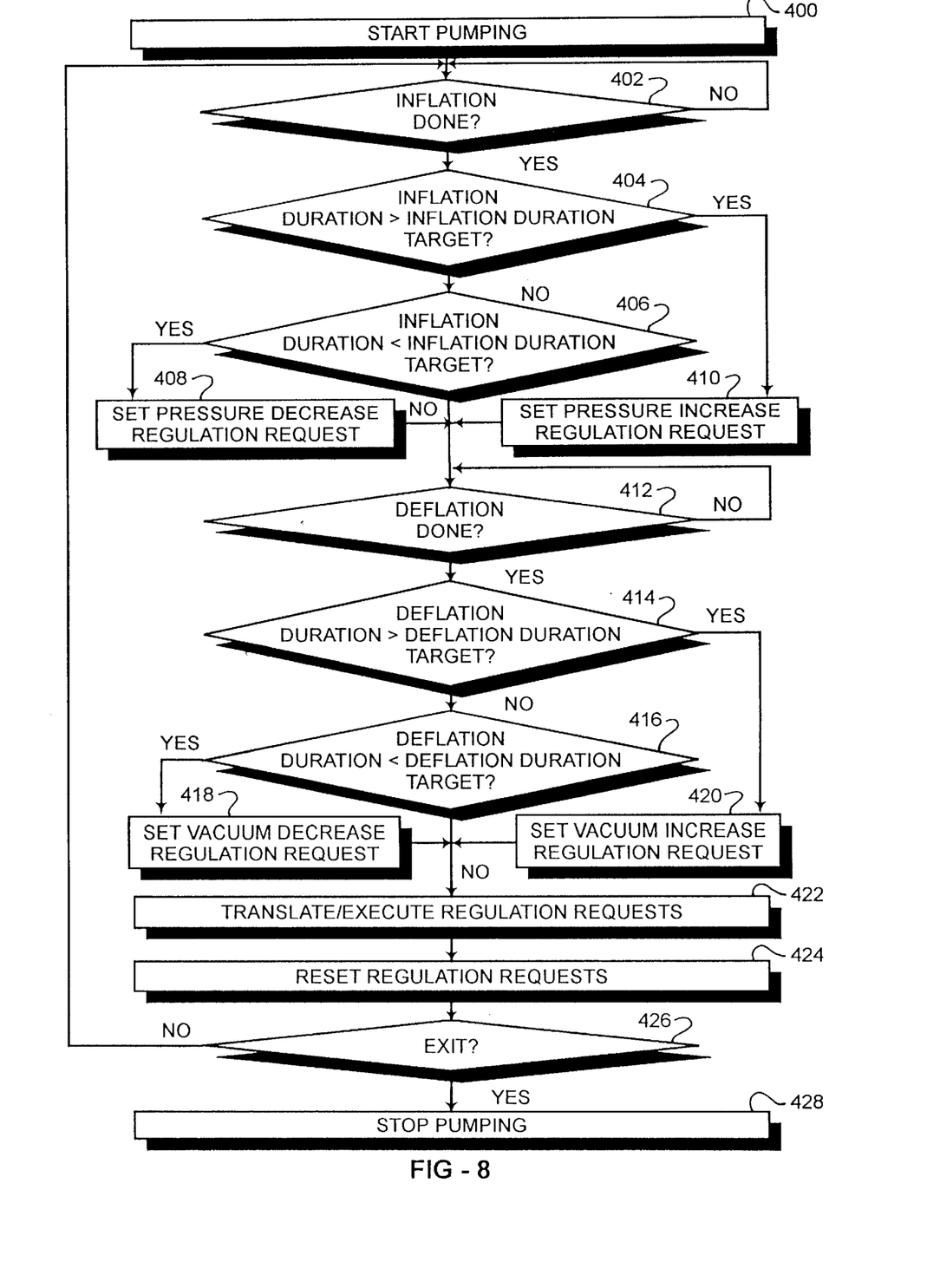
FIG. 8 is a simplified flow chart illustrating an alternative routine to adjust pressure in a positive pressure reservoir to drive fluid to the cardiac assist device.

FIG. 8 is a simplified flow chart illustrating a routine to adjust pressure in the fluid drive for the cardiac assist device. The routine of FIG. 8 improves the efficiency by reducing energy consumption of the previously described pressure control system for the cardiac assist device. The control routine illustrated in steps 400 through 428 implements a pressure/vacuum regulation algorithm which keeps pressure and vacuum at minimum levels necessary for efficient pumping, thereby providing the minimum level of power consumption. The pressure/vacuum regulation is done on a cyclical basis, where each regulation cycle is equal to and based on a complete pumping cycle. Conceptually, the regulation cycle includes two parts: first, generating regulation requests; and second, translating the regulation requests into system regulation actions. The generation of regulation requests is based on a comparison of actual inflation duration (ID) and actual deflation duration (DD) against target values corresponding to an inflation duration target (id) and deflation duration target (dd), which are chosen according to the physiological considerations to provide safe and efficient pumping.

Pumping is started in step 400. A first query is applied in step 402 to determine if inflation is completed. If inflation is not completed in step 402, the program recycles through step 402 until inflation is done. At that point, a second query is applied in step 404 to determine if the actual inflation duration was greater than the inflation duration target. If the answer to the query in step 404 is yes, the control routine branches to step 410 where it sets the pressure increase regulation request flag (pressure +). If the answer to the query in step 404 is no, the control routine continues to step 406 where a third query is applied to determine if the actual inflation duration is less than the inflation duration target. If the answer to the query in step 406 is yes, the control routine branches to step 408 where the program sets the pressure decrease regulation request flag (pressure −). If the answer to the query in step 406 is no, the control routine continues on to a fourth query in step 412. Steps 402 through 410 correspond to the portion of the control program setting the regulation request flags for the inflation or pressure portion of the pumping cycle.

Steps 412 through 420 correspond to setting the regulation request flags for the deflation or vacuum portion of the pumping cycle. In step 412, a fourth query is applied to determine if deflation is completed. If the answer to the query in step 412 is no, the control routine recycles through step 412 until deflation is done. When the answer to the query applied in step 412 is yes, the control program continues on to a fifth query applied in step 414. The fifth query of step 414 determines if the actual deflation duration is greater than the deflation duration target. If the answer to the query in step 414 is yes, the control routine branches to step 420 where it sets the vacuum increase regulation request flag (vacuum +). If the answer to the query in step 414 is no, the control program continues to a sixth query in step 416 to determine if the actual deflation duration was less than the deflation duration target. If the answer to the query applied in step 416 is yes, the control routine branches to step 418 where the program sets the vacuum decrease regulation request flag (vacuum −). If the answer to the query applied in step 416 is no, the program continues to step 422.

When inflation is completed, the actual inflation duration is compared against the inflation duration target value. If the actual inflation duration exceeds its target, it means that inflation is taking too long and the pressure should be increased to make the duration time shorter. The request to increase pressure is generated as a result. Oppositely, if the actual inflation duration is less than the inflation duration target value, it means that the inflation duration is too short and the pressure should be decreased to make the duration time longer, so the request to decrease pressure is generated. On completing deflation, the same logic applies to the actual deflation duration and the deflation duration target to generate either a decrease vacuum regulation request or an increase vacuum regulation request, where an excessively long deflation duration generates an increase vacuum request and an excessively short deflation duration generates a decrease vacuum request. Once the pressure and vacuum regulation requests are generated, the requests are translated in step 422 to the appropriate regulation actions which change the pressure/vacuum system condition, so that the next pumping cycle inflation and deflation durations should be closer to the inflation and deflation duration target values.

The description of the control program action in translating the generated regulation requests to the appropriate regulation actions is best summarized in the following table which uses the numbering reference numerals from FIG. 3. It should be recognized that it is expected that the control program of FIG. 8 can be modified by eliminating the vacuum regulation requests and corresponding actions in order to adapt the control program for use with the cardiac assist device illustrated in FIG. 4, if desired.

TABLE 1

| Pressure | | Vacuum | | |
|---|---|---|---|---|
| + | − | + | − | System Regulation Actions |
|   | X | X |   | Open pressure relief valve 56 |
| X |   | X |   | Increase compressor 28 motor speed |
|   | X |   | X | Decrease compressor 28 motor speed |
| X |   |   | X | Open vacuum relief valve 62 |
|   |   |   | X | Open vacuum relief valve 62 and simultaneously decrease compressor 28 motor speed |
|   |   | X |   | Open pressure relief valve 56 and simultaneously increase compressor 28 motor speed |
|   | X |   |   | Open pressure relief valve 56 and simultaneously decrease compressor 28 motor speed |
| X |   |   |   | Open vacuum relief valve 62 and simultaneously increase compressor 28 motor speed |
|   |   |   |   | No regulation action is necessary |

Referring now to Table 1, if the decrease pressure flag (pressure −) and the increase vacuum flag (vacuum +) are both set by the time the control program reaches step 422, the pressure relief valve 56 is opened to relieve some air from the system, so pressure in reservoir 44 will be decreased and vacuum in reservoir 46 will be increased. If the increase pressure flag (pressure +) and the increase vacuum flag (vacuum +) are both set, the motor speed of the compressor 28 is increased to increase the pressure in reservoir 44 and increase the vacuum in reservoir 46. If the decrease pressure flag (pressure −) and the decrease vacuum flag (vacuum −) are both set, the motor speed of the compressor 28 is decreased to decrease the pressure in reservoir 44 and decrease the vacuum in reservoir 46. If the increase pressure flag (pressure +) and the decrease vacuum flag (vacuum −) are both set, the vacuum relief valve 62 is opened to add some air into the system, so that pressure in reservoir 44 will be increased and vacuum in reservoir 46 will be decreased. If only the decrease vacuum flag (vacuum −) is set, the relief valve 62 is opened to add air into the system, so that pressure in reservoir 44 will be increased and vacuum in reservoir 46 will be decreased and simultaneously the motor speed of compressor 28 is decreased to additionally decrease vacuum in reservoir 46 and decrease pressure in reservoir 44. This combination of steps offset, or cancel out, the pressure increase due to the opening of the vacuum relief valve 62. If only the increase vacuum flag (vacuum +) is set, the pressure relief valve 56 is opened to relieve some air from the system, so that pressure in reservoir 44 will be decreased and vacuum in reservoir 46 will be increased, and simultaneously the motor speed of compressor 28 is increased to additionally increase vacuum in reservoir 46 and increase pressure in reservoir 44. The combination of these two steps offset, or cancel out, the previous pressure decrease due to the opening of pressure relief valve 56. If only the decrease pressure flag (pressure −) is set, the pressure relief valve 56 is opened to relieve some air from the system, so that pressure in reservoir 44 will be decreased and vacuum in reservoir 46 will be increased, and simultaneously the motor speed of compressor 28 is decreased to additionally decrease pressure in reservoir 44 and also decrease vacuum in reservoir 46. This combination of steps will offset, or cancel out, the previous vacuum increase due to opening the pressure relief valve 56. If only the increase pressure flag (pressure +) is set, the vacuum relief valve 62 is opened to add some air into the system, so that pressure in reservoir 44 will be increased and vacuum in reservoir 46 will be decreased, and simultaneously the motor speed of compressor 28 is increased to additionally increase pressure in reservoir 44 and also increase vacuum in reservoir 46. This combination of steps offsets, or cancels out the previous vacuum decrease due to the opening of vacuum relief valve 62. If none of the regulation request flags are set, no changes are required to the system operating parameters. After completion of the translation and execution of the regulation request flags in step 422, the control program proceeds to the reset regulation request flags in step 424. After resetting all flags, the control routine continues to the query of step 426 to determine if the control program should exit. If the answer to the query of step 426 is no, the control program recycles to a position just prior to the query of step 402. If the answer to the query of step 426 is yes, the control program proceeds to step 428 to stop pumping.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for controlling a cardiac assist device having an inflatable chamber operably positionable with respect to an aorta of a patient comprising the steps of:
    measuring an actual time interval required to inflate the inflatable chamber to a predetermined volume;
    comparing the actual time interval to a target time interval; and
    controlling pressure within a high pressure reservoir connectible to the inflatable chamber based on results of the comparing step.

2. The method of claim 1 wherein the time interval measuring step further comprises the steps of:
    determining differential pressure across an open control valve leading to the inflatable chamber;
    accumulating the differential pressure values with respect to time to obtain an accumulated value corresponding to an actual volume of pressurized fluid passing through the control valve to inflate the inflatable chamber;
    comparing the accumulated value to a target value; and
    when the accumulated value is at least equal to the target value, determining the actual time interval required to inflate the inflatable chamber.

3. The method of claim 1 wherein the controlling step further comprises the step of:
    if the actual time interval is greater than the target time interval, increasing pressure within the high pressure reservoir.

4. The method of claim 3 wherein the pressure increasing step further comprises the step of:
    opening a normally closed valve connected to a low pressure reservoir in a generally closed loop fluid drive system to correspondingly increase pressure in the high pressure reservoir.

5. The method of claim 3 wherein the pressure increasing step further comprises the step of:
    applying higher voltage to a DC powered motor to increase pressure output of a battery powered compressor connected to the high pressure reservoir in an open loop fluid drive system.

6. The method of claim 1 wherein the controlling step further comprises the step of:
    if the actual time interval is less than the target time interval, decreasing the pressure within the high pressure reservoir.

7. The method of claim 6 wherein the pressure decreasing step further comprises the step of:
    opening a normally closed valve connected to the high pressure reservoir to expel pressurized fluid to atmosphere.

8. The method of claim 1 wherein the comparing step further comprises the steps of:
    comparing the actual time interval to a predetermined minimum acceptable value;
    if the actual time interval is less than the minimum acceptable value, decreasing pressure in the high pressure reservoir;
    if the actual time interval is at least as great as the minimum acceptable value, comparing the actual time interval to a predetermined maximum acceptable value;
    if the actual time interval is greater than the maximum acceptable value, increasing pressure in the high pressure reservoir; and
    if the actual time interval is at most equal to the maximum acceptable value, maintaining current pressure in the high pressure reservoir.

9. An apparatus for controlling a cardiac assist device having an inflatable chamber operably positionable with respect to an aorta of a patient comprising:
    means for measuring an actual time interval required to inflate the inflatable chamber to a predetermined volume;
    means for comparing the actual time interval to a target time interval; and
    means for controlling pressure within a high pressure reservoir connectible to the inflatable chamber based on results of the comparing means.

10. The apparatus of claim 9 wherein the time interval measuring means further comprises:
    means for determining differential pressure across an open control valve leading to the inflatable chamber;
    means for accumulating the differential pressure values with respect to time to obtain an accumulated value corresponding to an actual volume of pressurized fluid passing through the control valve to inflate the inflatable chamber;
    means for comparing the accumulated value to a target value; and
    means for determining the actual time interval required to inflate the inflatable chamber when the accumulated value is at least equal to the target value.

11. The apparatus of claim 9 further comprising:

means for increasing pressure within the high pressure reservoir if the actual time interval is greater than the target time interval.

12. The apparatus of claim 11 wherein the pressure increasing means further comprises:

means for opening a normally closed valve connected to a low pressure reservoir in a generally closed loop fluid drive system to correspondingly increase pressure in the high pressure reservoir.

13. The apparatus of claim 11 wherein the pressure increasing means further comprises:

means for applying higher voltage to a DC powered motor to increase pressure output of a battery powered compressor connected to the high pressure reservoir in an open loop fluid drive system.

14. The apparatus of claim 9 wherein the controlling means further comprises:

means for decreasing the pressure within the high pressure reservoir if the actual time interval is less than the target time interval.

15. The apparatus of claim 14 wherein the pressure decreasing means further comprises:

means for opening a normally closed valve connected to the high pressure reservoir to expel pressurized fluid to atmosphere.

16. The apparatus of claim 9 wherein the comparing means further comprises:

means for comparing the actual time interval to a predetermined minimum acceptable value;

means for decreasing pressure in the high pressure reservoir connectible to the inflatable chamber during inflation cycles if the actual time interval is less than the minimum acceptable value;

means for comparing the actual time interval to a predetermined maximum acceptable value if the actual time interval is at least as great as the minimum acceptable value;

means for increasing pressure in the high pressure reservoir if the actual time interval is greater than the maximum acceptable value; and means for maintaining current pressure in the high pressure reservoir if the actual time interval is at most equal to the maximum acceptable value.

17. The apparatus of claim 9 further comprising:

means for controlling a cardiac assist device having an inflatable chamber operably positionable in an aorta of a patient including the steps of:

measuring an actual time interval required to inflate the inflatable chamber to a predetermined volume;

comparing the actual time interval to a target time interval; and controlling pressure within a pressure reservoir connectible to the inflatable chamber based on results of the comparing step.

18. A method for controlling a cardiac assist device having an inflatable chamber operably positionable with respect to an aorta of a patient comprising the steps of:

measuring an actual flow duration time required to move a predetermined volume of fluid with respect to the inflatable chamber through an open aperture of a control valve;

comparing the actual flow duration time to a target flow duration time; and selectively generating at least one control signal based on the comparing step to influence a subsequent flow duration time.

19. The method of claim 18, wherein the generating step further comprises the step of:

if the actual flow duration time for inflation is greater than the target flow duration time for inflation, performing at least one of the following steps:

generating the control signal to open a normally closed valve communicating with a low pressure reservoir connected in a generally closed loop fluid drive system to a high pressure reservoir through a variable speed compressor to increase pressure in the high pressure reservoir; and generating the control signal to increase speed of the variable speed compressor to increase pressure in the high pressure reservoir.

20. The method of claim 18, wherein the generating step further comprises the step of:

if the actual flow duration time for inflation is less than the target flow duration time for inflation, performing at least one of the following steps:

generating the control signal to open a normally closed valve communicating with a high pressure reservoir to decrease pressure in the high pressure reservoir; and generating the control signal to decrease speed of the variable speed compressor to decrease pressure in the high pressure reservoir.

21. The method of claim 18 further comprising:

said measuring step for measuring actual flow duration time for inflation and deflation of the inflatable chamber through the open aperture of the control valve;

said comparing step for comparing actual flow duration times for inflation and deflation to target flow duration times for inflation and deflation; and said generating step for generating control signals based on results of comparing the actual flow duration times for inflation and deflation with target flow duration times for inflation and deflation.

22. The method of claim 18, wherein the generating step further comprises the step of:

if the actual flow duration time for deflation is greater than the target flow duration time for deflation, performing at least one of the following steps:

generating the control signal to open a normally closed valve communicating with a high pressure reservoir connected in a generally closed loop fluid drive system to a low pressure reservoir through a variable speed compressor to increase vacuum in the low pressure reservoir; and generating the control signal to increase speed of the variable compressor to increase vacuum in the low pressure reservoir.

23. The method of claim 18, wherein the generating step further comprises the step of:

if the actual flow duration time for deflation is less than the target flow duration time for deflation, performing at least one of the following steps:

generating the control signal to open a normally closed valve communicating with a low pressure reservoir to decrease vacuum in the low pressure reservoir; and generating the control signal to decrease speed of the variable speed compressor to decrease vacuum in the low pressure reservoir.

24. An apparatus for controlling a cardiac assist device having an inflatable chamber operably positionable with respect to an aorta of a patient comprising:

means for measuring an actual flow duration time required to move a predetermined volume with respect to the inflatable chamber through an open aperture of a control valve;

means for comparing the actual flow duration time to a target flow duration time; and     means for selectively generating at least one control signal based on results of the comparing means to influence a subsequent flow duration time.

25. The apparatus of claim 24, wherein the generating means further comprises:

if the actual flow duration time for inflation is greater than the target flow duration time for inflation, means for performing at least one of the following functions:

generating the control signal to open a normally closed valve communicating with a low pressure reservoir connected in a generally closed loop fluid drive system to a high pressure reservoir through a variable speed compressor to increase pressure in the high pressure reservoir; and     generating the control signal to increase speed of the variable speed compressor to increase pressure in the high pressure reservoir.

26. The apparatus of claim 24, wherein the generating means further comprises:

if the actual flow duration time for inflation is less than the target flow duration time for inflation, means for performing at least one of the following functions:

generating the control signal to open a normally closed valve communicating with a high pressure reservoir to decrease pressure in the high pressure reservoir; and     generating the control signal to decrease speed of the variable speed compressor to decrease pressure in the high pressure reservoir.

27. The apparatus of claim 24 further comprising:

said measuring means for measuring actual flow duration times for inflation and deflation of the inflatable chamber through an open aperture of a control valve;

said comparing means for comparing the actual flow duration times for inflation and deflation to target flow duration times for inflation and deflation; and     said generating means for generating control signals based on results of comparing the actual flow duration times for inflation and deflation with respect to the target flow duration times for inflation and deflation.

28. The apparatus of claim 24, wherein the generating means further comprises:

if the actual flow duration time for deflation is greater than the target flow duration time for deflation, means for performing at least one of the following functions:

generating the control signal to open a normally closed valve communicating with a high pressure reservoir connected in a generally closed loop fluid drive system to a low pressure reservoir through a variable speed compressor to increase vacuum in the low pressure reservoir; and     generating the control signal to increase speed of the variable compressor to increase vacuum in the low pressure reservoir.

29. The apparatus of claim 24, wherein the generating means further comprises:

if the actual flow duration time for deflation is less than the target flow duration time for deflation, means for performing at least one of the following functions:

generating the control signal to open a normally closed valve communicating with a low pressure reservoir to decrease vacuum in the low pressure reservoir; and     generating the control signal to decrease speed of the variable speed compressor to decrease vacuum in the low pressure reservoir.

30. The apparatus of claim 24 wherein the generating means further comprises:

means for controlling pressure in a generally closed loop fluid drive system having a low pressure reservoir connected to a high pressure reservoir through a variable speed compressor for inflating the inflatable chamber through an isolation chamber, such that increasing pressure in the high pressure reservoir reduces subsequent flow duration time for inflation and decreasing pressure in the high pressure reservoir increases subsequent flow duration time for inflation.

31. The apparatus of claim 24 wherein the generating means further comprises:

means for controlling pressure in an open loop fluid drive system having a direct current powered motor driving a variable speed compressor to control pressure in a high pressure reservoir for inflating the inflatable chamber, such that increasing voltage to the direct current powered motor reduces subsequent flow duration time for inflation and decreasing voltage to the direct current powered motor increases subsequent flow duration time for inflation.

* * * * *